United States Patent [19]
Baker

[11] Patent Number: 5,856,279
[45] Date of Patent: Jan. 5, 1999

[54] ACYLATED NITROGEN COMPOUNDS USEFUL AS ADDITIVES FOR LUBRICATING OIL AND FUEL COMPOSITIONS

[75] Inventor: Mark R. Baker, Lyndhurst, Ohio

[73] Assignee: The Lubrizol Corporation, Wickliffe, Ohio

[21] Appl. No.: 81,424

[22] Filed: May 19, 1998

Related U.S. Application Data

[62] Division of Ser. No. 694,139, Aug. 8, 1996, Pat. No. 5,779,742.

[51] Int. Cl.$^6$ ............................ C10M 159/12; C10L 1/22
[52] U.S. Cl. .............................. 508/222; 44/330; 44/335; 44/386; 508/305; 508/454; 564/201; 564/204
[58] Field of Search .................................. 508/222, 305, 508/454; 44/330, 386, 347, 335; 564/204, 201

[56] References Cited

U.S. PATENT DOCUMENTS

| | | | |
|---|---|---|---|
| 3,172,892 | 3/1965 | LeSuer et al. | 260/326.5 |
| 3,215,707 | 11/1965 | Rense | 260/326.5 |
| 3,248,187 | 4/1966 | Bell | 44/63 |
| 3,259,578 | 7/1966 | Dickson et al. | 252/34 |
| 3,261,782 | 7/1966 | Anderson et al. | 252/57 |
| 3,269,946 | 8/1966 | Wiese | 252/32.5 |
| 3,454,617 | 7/1969 | Le Suer et al. | 260/408 |
| 3,954,808 | 5/1976 | Elliott et al. | 260/343.2 R |
| 3,966,807 | 6/1976 | Elliott et al. | 260/559 D |
| 4,046,802 | 9/1977 | Elliott et al. | 560/61 G |
| 4,051,049 | 9/1977 | Elliott et al. | 252/51.5 A |
| 4,083,791 | 4/1978 | Elliott et al. | 252/51.5 A |
| 4,108,784 | 8/1978 | Bryant | 252/56 R |
| 4,194,886 | 3/1980 | Ripple | 44/70 |
| 4,205,960 | 6/1980 | Bryant | 44/68 |
| 4,234,435 | 11/1980 | Meinhardt | 252/51.5 A |
| 4,285,824 | 8/1981 | Bryant | 252/56 |
| 4,412,031 | 10/1983 | Kitahara et al. | 524/526 |
| 4,412,041 | 10/1983 | Kitahara et al. | 525/154 |
| 4,512,903 | 4/1985 | Schlicht et al. | 252/51.5 A |
| 4,525,541 | 6/1985 | Kitahara et al. | 525/337 |
| 4,654,435 | 3/1987 | Kitahara et al. | 560/61 |
| 4,670,021 | 6/1987 | Nelson et al. | 44/66 |
| 4,704,427 | 11/1987 | Kitahara et al. | 524/531 |
| 5,137,980 | 8/1992 | De Gonia et al. | 525/327.6 |
| 5,336,278 | 8/1994 | Adams et al. | 44/419 |
| 5,458,793 | 10/1995 | Adams et al. | 252/47 |
| 5,620,949 | 4/1997 | Baker | 508/452 |
| 5,696,060 | 12/1997 | Baker et al. | 508/222 |
| 5,696,067 | 12/1997 | Adams | 508/476 |
| 5,779,742 | 7/1998 | Baker | 44/330 |

FOREIGN PATENT DOCUMENTS

| | | |
|---|---|---|
| 331556A2 | 6/1989 | European Pat. Off. . |
| 0623631 | 11/1994 | European Pat. Off. . |
| 0624638 | 11/1994 | European Pat. Off. . |
| 2103686 | 8/1972 | Germany . |
| 31488 | 11/1995 | WIPO . |

*Primary Examiner*—Margaret Medley
*Attorney, Agent, or Firm*—Joseph P. Fischer; James L. Cordek

[57] ABSTRACT

A process for reacting certain carboxylic reactants and at least one aldehyde or ketone with olefinic compounds then reacting the product prepared thereby with ammonia, a hydrazine or an amine, products prepared thereby and, additive concentrates, lubricating oil and fuel compositions.

36 Claims, No Drawings

ACYLATED NITROGEN COMPOUNDS USEFUL AS ADDITIVES FOR LUBRICATING OIL AND FUEL COMPOSITIONS

This is a divisional of application Ser. No. 08/694,139 filed Aug. 8, 1996 now U.S. Pat. No. 5,779,742.

FIELD OF THE INVENTION

This invention relates to acylated nitrogen compounds which are useful as low chlorine containing additives for lubricating oils and normally liquid fuels and a process for preparing the compounds.

BACKGROUND OF THE INVENTION

Numerous types of additives are used to improve lubricating oil and fuel compositions. Such additives include, but are certainly not limited to dispersants and detergents of the ashless and ash-containing variety, oxidation inhibitors, anti-wear additives, friction modifiers, and the like. Such materials are well known in the art and are described in many publications, for example, Smalheer, et al, "Lubricant Additives", Lezius-Hiles Co., Cleveland, Ohio, U.S.A. (1967); M. W. Ranney, Ed., "Lubricant Additives", Noyes Data Corp., Park Ridge, N.J., U.S.A. (1973); M. J. Satriana, Ed., "Synthetic Oils and Lubricant Additives, Advances since 1977", Noyes Data Corp., Park Ridge N.J., U.S.A. (1982), W. C. Gergel, "Lubricant Additive Chemistry", Publication 694-320-65R1 of the Lubrizol Corp., Wickliffe, Ohio, U.S.A. (1994); and W. C. Gergel et al, "Lubrication Theory and Practice" Publication 794-320-59R3 of the Lubrizol Corp., Wickliffe, Ohio, U.S.A. (1994); and in numerous United States patents, for example Chamberlin, III, U.S. Pat. No. 4,326,972, Schroeck et al, U.S. Pat. No. 4,904,401, Blystone et al., U.S. Pat. No. 5,356,546 and Ripple et al, U.S. Pat. No. 4,981,602. Many such additives are frequently derived from carboxylic reactants, for example, acids, esters, anhydrides, lactones, and others. Specific examples of commonly used carboxylic compounds used as intermediates for preparing lubricating oil additives include alkyl- and alkenyl substituted succinic acids and anhydrides, polyolefin substituted carboxylic acids, aromatic acids, such as salicylic acids, and others. Illustrative carboxylic compounds are described in Meinhardt, et al, U.S. Pat. No. 4,234,435; Norman et al, U.S. Pat. No. 3,172,872; LeSuer et al, U.S. Pat. No. 3,454,607, and Rense, U.S. Pat. No. 3,215,707.

Many carboxylic intermediates used in the preparation of lubricating oil additives contain chlorine. While the amount of chlorine present is often only a very small amount of the total weight of the intermediate, the chlorine frequently is carried over into the carboxylic derivative which is desired as an additive. For a variety of reasons, including environmental reasons, government regulation, and commercial reasons the industry has been making efforts to reduce or to eliminate chlorine from additives designed for use as lubricant or fuel additives. The matter of chlorine content in additives is discussed in numerous patents including U.S. Pat. Nos. 5,356,552; 5,370,805; 5,445,657 and 5,454,964.

Accordingly, it is desirable to provide low chlorine or chlorine free additives for use in lubricants and fuels.

The present invention provides acylated nitrogen compounds which meet this requirement.

B. B. Snider and J. W. van Straten, J. Org. Chem., 44, 3567–3571 (1979) describe certain products prepared by the reaction of methyl glyoxylate with several butenes and cyclohexenes. K. Mikami and M. Shimizu, Chem. Rev., 92, 1021–1050 (1992) describe carbonyl-ene reactions, including glyoxylate-ene reactions. D. Savostianov (communicated by P. Pascal), C.R. Acad. Sc. Paris, 263, (605–7) (1966) relates to preparation of some α-hydroxylactones via the action of glyoxylic acid on olefins. M. Kerfanto et. al., C.R. Acad. Sc. Paris, 264, (232–5) (1967) relates to condensation reactions of α-α-di-(N-morpholino)acetic acid and glyoxylic acid with olefins. B. B. Jarvis et al, Synthesis, 1079–82 (1990) relates to reactions of oxocarboxylic acids with olefins under acidic conditions to give α-hydroxy butyrolactones.

Fuels containing additives to improve the performance thereof are described in numerous patents including the following U.S. Pat. Nos.:

| | |
|---|---|
| 4,071,327 | 5,336,278 |
| 4,379,065 | 5,356,546 |
| 4,400,178 | 5,458,793 |
| 4,564,460 | |

SUMMARY OF THE INVENTION

The present invention provides a process comprising first reacting, optionally in the presence of an acidic catalyst selected from the group consisting of organic sulfonic acids, heteropolyacids, Lewis acids, and mineral acids, (A) at least one olefinic compound containing at least one group of the formula $$\underset{/}{\overset{\backslash}{\phantom{x}}}C{=}C{-}\overset{|}{\underset{|}{C}}H \qquad (I)$$

and (B) at least one carboxylic reactant selected from the group consisting of compounds of the formula $$R^3C(O)(R^4)_nC(O)OR^5 \qquad (IV)$$

and compounds of the formula $$R^3{-}\underset{\underset{R^9O}{|}}{\overset{\overset{R^9O}{|}}{C}}{-}(R^4)_n{-}C(O)OR^5 \qquad (V)$$

wherein each of $R^3$, $R^5$ and each $R^9$ is independently H or a hydrocarbyl group, $R^4$ is a divalent hydrocarbylene group, and n is 0 or 1 in amounts ranging from 0.6 moles (B) per mole of (A) to 1.5 moles (B) per equivalent of (A); from about 0.5 to about 2 moles, per mole of (B), of (C) at least one aldehyde or ketone; then reacting the product formed thereby with from about 0.5 equivalents up to about 2 moles, per mole of (B) of at least one of (D) ammonia or a hydrazine or an amine characterized by the presence within its structure of at least one H—N group and products prepared by this process.

Also provided are additive concentrates for preparing lubricating oil and fuel compositions, lubricating oil compositions and fuel compositions.

DETAILED DESCRIPTION OF THE PREFERRED EMBODIMENTS

As used herein, the terms "hydrocarbon", "hydrocarbyl" or "hydrocarbon based" mean that the group being described has predominantly hydrocarbon character within the context of this invention. These include groups that are purely hydrocarbon in nature, that is, they contain only carbon and hydrogen. They may also include groups containing non-hydrocarbon substituents or atoms which do not alter the predominantly hydrocarbon character of the group. Such substituents may include halo-, alkoxy-, nitro-, etc. These groups also may contain hetero atoms. Suitable hetero atoms will be apparent to those skilled in the art and include, for example, sulfur, nitrogen and oxygen. Therefore, while remaining predominantly hydrocarbon in character within the context of this invention, these groups may contain atoms other than carbon present in a chain or ring otherwise composed of carbon atoms.

In general, no more than about three non-hydrocarbon substituents or hetero atoms, and preferably no more than one, will be present for every 10 carbon atoms in the hydrocarbon, hydrocarbyl or hydrocarbon based groups. Most preferably, the groups are purely hydrocarbon in nature, that is they are essentially free of atoms other than carbon and hydrogen.

Throughout the specification and claims the expression soluble or dispersible is used. By soluble or dispersible is meant that an amount needed to provide the desired level of activity or performance can be incorporated by being dissolved, dispersed or suspended in an oil of lubricating viscosity or in a normally liquid fuel. Usually, this means that at least about 0.001% by weight of the material can be incorporated in a lubricating oil or normally liquid fuel. For a further discussion of the terms oil soluble and dispersible, particularly "stably dispersible", see U.S. Pat. No. 4,320,019 which is expressly incorporated herein by reference for relevant teachings in this regard.

As noted hereinabove, provided by this invention are certain acylated nitrogen compounds and a process for preparing low chlorine or chlorine free compositions useful as low chlorine or chlorine free additives for lubricating oil and fuel compositions.

The Process

In one embodiment, the present invention relates to a process comprising first reacting, optionally in the presence of an acidic catalyst selected from the group consisting of organic sulfonic acids, heteropolyacids, Lewis acids, and mineral acids, (A) at least one olefinic compound containing at least one group of the formula

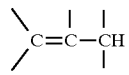 (I)

and (B) at least one carboxylic reactant selected from the group consisting of compounds of the formula $R^3C(O)(R^4)_nC(O)OR^5$ (IV)

and compounds of the formula

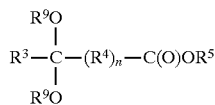 (V)

wherein each of $R^3$, $R^5$ and each $R^9$ is independently H or a hydrocarbyl group, $R^4$ is a divalent hydrocarbylene group, and n is 0 or 1 in amounts ranging from 0.6 moles (B) per mole of (A) to 1.5 moles (B) per equivalent of (A); from about 0.5 to about 2 moles, per mole of (B), of (C) at least one aldehyde or ketone, then reacting the product formed thereby with from about 0.5 equivalents up to about 2 moles, per mole of (B) of at least one of (D) ammonia or a hydrazine or an amine characterized by the presence within its structure of at least one H—N group.

Reactants (A), (B), and (C) may be present at the outset of the reaction or (A) and (B) may be reacted first followed by reaction with (C). Under these conditions, all of (A) and (B) may be present at the same time; however, it has been found that improvements in yield and purity of the product arising from the reaction of (A) and (B) may be attained when the carboxylic reactant (B) is added to the olefinic compound (A) either portionwise or continuously over an extended period of time, usually up to about 10 hours, more often from 1 hour up to about 6 hours, frequently from about 2 to about 4 hours.

The first step of the process may be conducted in the presence of an azeotroping solvent. Well known azeotroping solvents include toluene, xylene, cyclohexane, etc. Cyclohexane is preferred.

The Catalyst

The first step of the process of this invention is optionally conducted in the presence of an acidic catalyst. Acid catalysts, such as organic sulfonic acids, for example, para-toluene sulfonic acid, methane sulfonic acid and sulfonated polymers such as those marketed under the tradename Amberlyst® (Rohm & Haas), heteropolyacids, the complex acids of heavy metals (e.g., Mo, W, Sn, V, Zr, etc.) with phosphoric acids (e.g., phosphomolybdic acid), and mineral acids, for example, $H_2SO_4$ and phosphoric acid, are useful. The amount of catalyst used is generally small, ranging from about 0.01 mole % to about 10 mole %, more often from about 0.1 mole % to about 2 mole %, based on moles of olefinic reactant.

(A) The Olefinic Compound

The olefinic compound employed as a reactant in the process of this invention contains at least one group of the formula

 (I)

and has the general formula $(R^1)(R^2)C=C(R^6)(CH(R^7)(R^8))$ (III)

wherein each of $R^1$ and $R^2$ is, independently, hydrogen or a hydrocarbon based group. Each of $R^6$, $R^7$ and $R^8$ is, independently, hydrogen or a hydrocarbon based group; preferably at least one is a hydrocarbon based group containing at least 7 carbon atoms. These olefinic compounds are diverse in nature.

Virtually any compound containing an olefinic bond may be used provided it meets the general requirements set forth hereinabove for (III) and does not contain any functional groups (e.g., primary or secondary amines) that would interfere with the carboxylic reactant (B). Useful olefinic compounds may be terminal olefins, i.e., olefins having a $H_2C=C$ group, or internal olefins. Useful olefinic compounds may have more than one olefinic bond, i.e., they may be dienes, trienes, etc. Most often they are mono-olefinic. Examples include linear α-olefins, cis- or trans- disubstituted olefins, trisubstituted olefins and tetrasubstituted olefins.

When (A) is a monoolefinic, one mole of (A) contains one equivalent of C=C; when (A) is diolefinic, one mole of (A) contains 2 equivalents of C=C bonds; when (A) is triolefinic, one mole of (A) contains 3 equivalents of C=C bonds, and so forth.

Aromatic double bonds are not considered to be olefinic double bonds within the context of this invention.

As used herein, the expression "polyolefin" defines a polymer derived from olefins. The expression "polyolefinic" refers to a compound containing more than one C=C bond.

Among useful compounds are those that are purely hydrocarbon, i.e., those substantially free of non-hydrocarbon groups, or they may contain one or more non-hydrocarbon groups as discussed in greater detail herein.

In one embodiment, the olefinic compounds are substantially hydrocarbon, that is, each R group in (III) is H or contains essentially carbon and hydrogen. In one aspect within this embodiment, each of $R^1$, $R^2$, $R^7$ and $R^8$ is hydrogen and $R^6$ is a hydrocarbyl group containing from 7 to about 5,000 carbon atoms, more often from about 30 up to about 200 carbon atoms, preferably from about 50 up to about 100 carbon atoms. In another aspect of this embodiment, each of $R^1$ and $R^2$ is hydrogen, $R^6$ is H or a lower alkyl group, especially methyl, and the group (CH$(R^7)(R^8)$) is a hydrocarbyl group containing from 7 to about 5,000 carbon atoms, more typically from about 30 up to about 200 carbon atom, preferably from 50 up to about 100 carbon atoms.

In another embodiment, one or more of the R groups present in (III) is an organic radical which is not purely hydrocarbon. Such groups may contain or may be groups such as carboxylic acid, ester, amide, salt, including ammonium, amine and metal salts, cyano, hydroxy, thiol, tertiary amino, nitro, alkali metal mercapto and the like. Illustrative of olefinic compounds (III) containing such groups are methyl oleate, oleic acid, 2-dodecenedioic acid, octene diol, linoleic acid and esters thereof, and the like.

Preferably, the hydrocarbyl groups are aliphatic groups. In one preferred embodiment, when an R group is an aliphatic group containing a total of from about 30 to about 100 carbon atoms, the olefinic compound is derived from homopolymerized and interpolymerized $C_{2-18}$ mono- and di-olefins, preferably 1-olefins. In a preferred embodiment, the olefins contain from 2 to about 5 carbon atoms, preferably 3 or 4 carbon atoms. Examples of such olefins are ethylene, propylene, butene-1, isobutylene, butadiene, isoprene, 1-hexene, 1-octene, etc. R groups can, however, be derived from other sources, such as monomeric high molecular weight alkenes (e.g. 1-tetracontene), aliphatic petroleum fractions, particularly paraffin waxes and cracked analogs thereof, white oils, synthetic alkenes such as those produced by the Ziegler-Natta process (e.g., poly-(ethylene) greases) and other sources known to those skilled in the art. Any unsaturation in the R groups may be reduced by hydrogenation according to procedures known in the art, provided at least one olefinic group remains as described for (III).

In one preferred embodiment, at least one R is derived from polybutene, that is, polymers of $C_4$ olefins, including 1-butene, 2-butene and isobutylene. Those derived from isobutylene, i.e., polyisobutylenes, are especially preferred. In another preferred embodiment, R is derived from polypropylene. In another preferred embodiment, R is derived from ethylene-alpha olefin polymers, including ethylene-α-olefin-diene polymers, especially those wherein the diene is a non-conjugated diene. Representative of such polymers are the ethylene-propylene copolymers and ethylene-propylene-diene terpolymers marketed under the Trilene® tradename by the Uniroyal Company. Molecular weights of such polymers may vary over a wide range, but especially preferred are those having number average molecular weights ($\overline{M}_n$) ranging from about 300 to about 20,000, preferably 700 to about 10,000, often from 900 to 2,500. In one preferred embodiment, the olefin is an ethylene-propylene-diene terpolymer having $\overline{M}_n$ ranging from about 900 to about 8,000, often up to about 2,000. Such materials are included among the Trilene® polymers marketed by the Uniroyal Company, Middlebury, Conn., U.S.A. and Ortholeum® 2052 marketed by the DuPont Company. Also contemplated are polydiene polymer, those prepared by polymerizing dienes.

Ethylene-alpha olefin copolymers and ethylene-lower olefin-diene terpolymers are described in numerous patent documents, including European patent publication EP 279, 863, Japanese patent publication 87-129,303 and the following U.S. Pat. Nos.:

| | |
|---|---|
| 3,598,738 | 4,357,250 |
| 4,026,809 | 4,658,078 |
| 4,032,700 | 4,668,834 |
| 4,137,185 | 4,937,299 |
| 4,156,061 | 5,324,800 |
| 4,320,019 | | each of which is incorporated herein by reference for relevant disclosures of these ethylene based polymers.

A preferred source of hydrocarbyl groups R are polybutenes obtained by polymerization of a $C_4$ refinery stream having a butene content of 35 to 75 weight percent and isobutylene content of 15 to 60 weight percent in the presence of a Lewis acid catalyst such as aluminum trichloride or boron trifluoride. These polybutenes contain predominantly (greater than 80% of total repeating units) isobutylene repeating units of the configuration

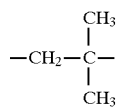

These polybutenes are typically monoolefinic, that is they contain but one olefinic bond per molecule.

The olefinic compound may be a polyolefin comprising a mixture of isomers wherein from about 50 percent to about 65 percent are tri-substituted olefins wherein one substituent contains from 2 to about 500 carbon atoms, often from about 30 to about 200 carbon atoms, more often from about 50 to about 100 carbon atoms, usually aliphatic carbon atoms, and the other two substituents are lower alkyl.

When the olefin is a tri-substituted olefin, it frequently comprises a mixture of cis- and trans-1-lower alkyl, 1-(aliphatic hydrocarbyl containing from 30 to about 100 carbon atoms), 2-lower alkyl ethene and 1,1-di-lower alkyl, 2-(aliphatic hydrocarbyl containing from 30 to about 100 carbon atoms) ethene.

In one embodiment, the monoolefinic groups are predominantly vinylidene groups, i.e., groups of the formula

especially those of the formula
although the polybutenes may also comprise other olefinic configurations.

In one embodiment the polybutene is substantially monoolefinic, comprising at least about 30 mole %, preferably at least about 50 mole % vinylidene groups, more often at least about 70 mole % vinylidene groups. Such materials and methods for preparing them are described in U.S. Pat. Nos. 5,071,919; 5,137,978; 5,137,980; 5,286,823 and 5,408,018, and in published European patent application EP 646103-A1, each of which is expressly incorporated herein by reference. They are commercially available, for example under the tradenames Ultravis (BP Chemicals) and Glissopal (BASF).

In one embodiment, the olefinic compound is a polyolefin comprising a mixture of isomers, at least about 50% by weight of the mixture comprising isomers of the formula $$H_2C=C(R^6)(CH(R^7)(R^8))$$

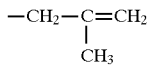

wherein $R^6$ is H or lower alkyl.

As is apparent from the foregoing, olefins of a wide variety of type and of molecular weight are useful for preparing the compositions of this invention. Useful olefins are usually substantially hydrocarbon and have number average molecular weight ranging from about 100 to about 70,000, more often from about 200 to about 7,000, even more often from about 1,300 to about 5,000, frequently from about 400 to about 3,000. Linear alpha-olefins containing from 7–100 carbon atoms, preferably from 8–50 carbons and offer from 8 to about 28 carbon atoms are useful.

Specific characterization of olefin reactants (A) used in the processes of this invention can be accomplished by using techniques known to those skilled in the art. These techniques include general qualitative analysis by infrared and determinations of average molecular weight, e.g., $\overline{M}_n$, number average molecular weight, and $\overline{M}_w$, weight average molecular weight, etc. employing vapor phase osmometry (VPO) and gel permeation chromatography (GPC). Structural details can be elucidated employing proton and carbon 13 ($C^{13}$) nuclear magnetic resonance (NMR) techniques. NMR is useful for determining substitution characteristics about olefinic bonds, and provides some details regarding the nature of the substituents. More specific details regarding substituents about the olefinic bonds can be obtained by cleaving the substituents from the olefin by, for example, ozonolysis, then analyzing the cleaved products, also by NMR, GPC, VPO, and by infra-red analysis and other techniques known to the skilled person.

(B) The Carboxylic Reactant

The carboxylic reactant is at least one member selected from the group consisting of compounds of the formula $$R^3C(O)(R^4)_nC(O)OR^5 \qquad (IV)$$

and compounds of the formula

wherein each of $R^3$, $R^5$ and each $R^9$ is independently H or a hydrocarbyl group.

$R^3$ is usually H or an aliphatic group, that is, alkyl or alkenyl, preferably allyl, more preferably lower alkyl. Especially preferred is where $R^3$ is H or methyl, most preferably, H.

$R^4$ is a divalent hydrocarbylene group. This group may be aliphatic or aromatic, but is usually aliphatic. Often, $R^4$ is an alkylene group containing from 1 to about 3 carbon atoms. The 'n' is 0 or 1; that is, in one embodiment $R^4$ is present and in another embodiment, $R^4$ is absent. More often, $R^4$ is absent.

When $R^5$ is hydrocarbyl, it is usually an aliphatic group, often a group containing from 1 to about 30 carbon atoms, often from 8 to about 18 carbon atoms. In another embodiment, $R^5$ is lower alkyl, wherein "lower alkyl" is defined hereinabove. Most often, $R^5$ is H or lower alkyl, especially methyl, ethyl, propyl and butyl.

$R^9$ is H or hydrocarbyl, preferably H or lower alkyl, especially methyl, ethyl, propyl and butyl.

Examples of carboxylic reactants (B) are glyoxylic acid, and other omega-oxoalkanoic acids, keto alkanoic acids such as pyruvic acid, levulinic acid, ketovaleric acids, ketobutyric acids, the hemiacetals, for example glyoxylic acid methyl ester methyl hemiacetal, and hemiketals thereof, and the corresponding acetals and ketals, and numerous others. The skilled worker, having the disclosure before him, will readily recognize the appropriate compound of formula (IV) and (V) to employ as a reactant to generate a given compound.

Reactant (B) may be a compound of the formula

wherein each of $R^3$ and $R^5$ is independently H alkyl. Such compounds arise when the carbonyl reactant is hydrated. Glyoxylic acid monohydrate is a representative example.

(C) The Aldehyde or Ketone

The aldehyde or ketone reactant employed in the process of this invention is a carbonyl compound other than a carboxy-substituted carbonyl compound. Accordingly, it is to be understood that it is not contemplated herein that reactant (C) includes any of the species defined hereinabove as reactant (B). Suitable compounds include those having the general formula RC(O)R', wherein R and R' are each, independently, H or a hydrocarbyl group as defined hereinabove. As noted in the description, hydrocarbyl groups may contain other groups or heteroatoms which do not interfere with the process and products of this invention. Preferably, reactant (C) contains from 1 to about 12 carbon atoms. Suitable aldehydes include formaldehyde, acetaldehyde, propionaldehyde, butyraldehyde, isobutyraldehyde, pentanal, hexanal, heptaldehyde, octanal, benzaldehyde, and higher aldehydes. Other aldehydes, such as dialdehydes, especially glyoxal, are useful, although monoaldehydes are generally preferred.

The most preferred aldehyde is formaldehyde, which can be supplied as the aqueous solution often referred to as formalin, but is more often used in the polymeric form as paraformaldehyde, which is a reactive equivalent of, or a source of, formaldehyde. Other reactive equivalents include hydrates or cyclic trimers.

Suitable ketones include acetone, butanone, methyl ethyl ketone, and other ketones. Preferably, one of the hydrocarbyl groups is methyl.

Mixtures of two or more aldehydes and/or ketones are also useful.

The process is conducted at temperatures ranging from ambient up to the lowest decomposition temperature of any of the reactants, usually from about 60° C. to about 220° C., more often from about 120° C. to about 180° C., preferably up to about 160° C. When the reaction is conducted in the presence of organic sulfonic acid or mineral acid catalyst, the reaction is usually conducted at temperatures up to about 160° C. The process employs from about 0.6 moles of reactant (B) per mole of olefinic compound (A), up to 1.5 moles (B) per equivalent of (A), more often from about 0.8 moles (B) per mole of (A) to about 1.2 moles (B) per equivalent of (A), even more often from about 0.95 moles (B) per mole of (A) to about 1.05 moles (B) per equivalent of (A). Reactant (C) is used in amounts ranging from about 0.5 to about 2 moles per mole of (B), preferably, from about 0.8 to about 1.5 moles per mole of (B), and most often from about 0.9 to about 1.1 moles per mole of (B). As noted herein, many reactants contain water which is removed. Removal of water at moderate temperatures is attainable employing reduced pressure, a solvent that aids in azeotropic distillation of water, or by purging with an inert gas such as $N_2$.

The progress of the first part of the reaction can be followed by observing the infra-red spectrum. The absorption for —COOH carbonyl of the products appears at about 1710 $cm_{-1}$. The total acid number as measured using essentially the procedure in ASTM D-664 (Potentiometric Method) or ASTM D-974 (Color Indicator Method) is useful together with the infrared, keeping in mind that non-acidic products (e.g., polyester products), those derived from non-acidic reactants and condensation products such as lactones will not display significant acid numbers.

These ASTM procedures appear in the Annual Book of ASTM Standards, Volume 05.01, ASTM, 1916 Race Street, Philadelphia, Pa., U.S.A.

(D) Ammonia, Hydrazine and Amine Reactants

Suitable (D) reactants, as defined herein, include ammonia, hydrazines, monoamines or polyamines. The (D) reactants must contain at least one N—H group. The monoamines generally contain from 1 to about 24 carbon atoms, preferably 1 to about 12, and more preferably 1 to about 6. Examples of monoamines useful in the present invention include primary amines, for example methylamine, ethylamine, propylamine, butylamine, octylamine, and dodecylamine. Examples of secondary amines include dimethylamine, diethylamine, dipropylamine, dibutylamine, methylbutylamine, ethylhexylamine, etc. Tertiary monoamines will not result in formation of an amide, but can form salts with carboxylic acids.

In another embodiment, the monoamine may be a hydroxyamine. Typically, the hydroxyamines are primary or secondary alkanolamines or mixtures thereof. As stated above, tertiary monoamines will not react to form amides; however tertiary alkanol monoamines sometimes can react to form a tertiary amino group containing ester. Alkanol amines that can react to form amide can be represented, for example, by the formulae:

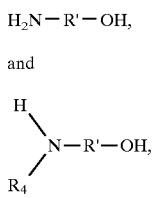

wherein each $R_4$ is independently a hydrocarbyl group of one to about 22 carbon atoms or hydroxyhydrocarbyl group of two to about 22 carbon atoms, preferably one to about four, and R' is a divalent hydrocarbyl group of about two to about 18 carbon atoms, preferably two to about four. The group —R'—OH in such formulae represents the hydroxyhydrocarbyl group. R' can be an acyclic, alicyclic or aromatic group. Typically, R' is an acyclic straight or branched alkylene group such as an ethylene, 1,2-propylene, 1,2-butylene, 1,2-octadecylene, etc. group. When two $R^4$ groups are present in the same molecule they can be joined by a direct carbon-to-carbon bond or through a heteroatom (e.g., oxygen, nitrogen or sulfur) to form a 5-, 6-, 7- or 8-membered ring structure. Examples of such heterocyclic amines include N-(hydroxyl lower alkyl)-morpholines, -thiomorpholines, -piperidines, -oxazolidines, -thiazolidines and the like. Typically, however, each $R^4$ is independently a methyl, ethyl, propyl, butyl, pentyl or hexyl group.

Examples of these alkanolamines include mono-, di-, and triethanolamine, diethylethanolamine, ethylethanolamine, butyldiethanolamine, etc.

The hydroxyamnines can also be ether N-(hydroxyhydrocarbyl) amines. These are hydroxy poly (hydrocarbyloxy) analogs of the above-described hydroxy amines (these analogs also include hydroxyl-substituted oxyalkylene analogs). Such N-(hydroxyhydrocarbyl) amines can be conveniently prepared, for example, by reaction of epoxides with aforedescribed amines and can be represented by the formulae:

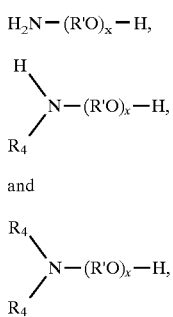

wherein x is a number from about 2 to about 15 and $R_4$ and R' are as described above. $R_4$ may also be a hydroxypoly (hydrocarbyloxy) group.

Other useful amines include ether amines of the general formula

wherein $R_6$ is a hydrocarbyl group, preferably an aliphatic group, more preferably an alkyl group, containing from 1 to about 24 carbon atoms, $R^1$ is a divalent hydrocarbyl group, preferably an allylene group, containing from two to about 18 carbon atoms, more preferably two to about 4 carbon atoms and $R_7$ is H or hydrocarbyl, preferably H or aliphatic, more preferably H or alky, more preferably H. When $R_7$ is not H, then it preferably is alkyl containing from one to about 24 carbon atoms. Especially preferred ether amines are those available under the name SURFAM produced and marketed by Sea Land Chemical Co., Westlake, Ohio.

The amine may also be a polyamine. The polyamine may be aliphatic, cycloaliphatic, heterocyclic or aromatic. Examples of the polyamines include alkylene polyamines, hydroxy containing polyamines, arylpolyamines, and heterocyclic polyamines.

Alkylene polyamines are represented by the formula

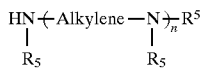

wherein n has an average value between about 1 and about 10, preferably about 2 to about 7, more preferably about 2 to about 5, and the "Alkylene" group has from 1 to about 10 carbon atoms, preferably about 2 to about 6, more preferably about 2 to about 4. $R_5$ is independently hydrogen or an aliphatic or hydroxy-substituted aliphatic group of up to about 30 carbon atoms. Preferably $R_5$ is H or lower alkyl, most preferably, H.

Alkylene polyamines include methylene polyamines, ethylene polyamines, butylene polyamines, propylene polyamines, pentylene polyamines, etc. Higher homologs and related heterocyclic amines such as piperazines and N-amino alkyl-substituted substituted piperazines are also included. Specific examples of such polyamines are ethylene diamine, diethylene triamine, triethylene tetramine, tris-(2-aminoethyl)amine, propylene diamine, trimethylene diamine, tripropylene tetramine, tetraethylene pentamine, hexaethylene heptamine, pentaethylenehexamine, aminoethyl piperazine, dimethyl aminopropylamine, etc.

Higher homologs obtained by condensing two or more of the above-noted alkylene amines are similarly useful as are mixtures of two or more of the aforedescribed polyamines.

Ethylene polyamines, such as some of those mentioned above, are preferred. They are described in detail under the heading Ethylene Amines in Kirk Othmer's "Encyclopedia of Chemical Technology", 2d Edition, Vol. 7, pages 22–37, Interscience Publishers, New York (1965). Such polyamines are most conveniently prepared by the reaction of ethylene dichloride with ammonia or by reaction of an ethylene imine with a ring opening reagent such as water, ammonia, etc. These reactions result in the production of a complex mixture of polyalkylene polyamines including cyclic condensation products such as the aforedescribed piperazines. Ethylene polyamine mixtures are useful.

Other useful types of polyamine mixtures are those resulting from stripping of the above-described polyamine mixtures to leave as residue what is often termed "polyamine bottoms". In general, alkylene polyamine bottoms can be characterized as having less than two, usually less than 1% (by weight) material boiling below about 200° C. A typical sample of such ethylene polyamine bottoms obtained from the Dow Chemical Company of Freeport, Tex., designated "E-100" has a specific gravity at 15.6° C. of 1.0168, a percent nitrogen by weight of 33.15 and a viscosity at 40° C. of 121 centistokes. Gas chromatography analysis of such a sample contains about 0.93% "Light Ends" (most probably diethylenetriamine), 0.72% triethylenetetramine, 21.74% tetraethylene pentaamine and 76.61% pentaethylene hexamine and higher (by weight). These alkylene polyamine bottoms include cyclic condensation products such as piperazine and higher analogs of diethylenetriamine, triethylenetetramine and the like.

Another useful polyamine is a condensation product obtained by reaction of at least one hydroxy compound with at least one polyamine reactant containing at least one primary or secondary amino group. The hydroxy compounds are preferably polyhydric alcohols and amines. Preferably the hydroxy compounds are polyhydric amines. Polyhydric amines include any of the above-described monoamines reacted with an alkylene oxide (e.g., ethylene oxide, propylene oxide, butylene oxide, etc.) having two to about 20 carbon atoms, preferably two to about four. Examples of polyhydric amines include tri-(hydroxypropyl) amine, tris-(hydroxymethyl)amino methane, 2-amino-2-methyl-1,3-propanediol, N,N,N',N'-tetrakis(2-hydroxypropyl) ethylenediamine, and N,N,N',N'-tetrakis(2-hydroxyethyl) ethylenediamine.

Polyamine reactants, which react with the polyhydric alcohol or amine to form the condensation products or condensed amines, are described above. Preferred polyamine reactants include triethylenetetramine (TETA), tetraethylenepentamine (TEPA), pentaethylenehexamine (PEHA), and mixtures of polyamines such as the above-described "amine bottoms".

The condensation reaction of the polyamine reactant with the hydroxy compound is conducted at an elevated temperature, usually about 60° C. to about 265° C. in the presence of an acid catalyst.

The amine condensates and methods of making the same are described in Steckel (U.S. Pat. No. 5,053,152) which is incorporated by reference for its disclosure to the condensates and methods of making.

In another embodiment, the polyamines are hydroxy-containing polyamines. Hydroxy-containing polyamine analogs of hydroxy monoamines, particularly alkoxylated alkylenepolyamines can also be used. Such polyamines can be made by reacting the above-described alkylene amines with one or more of the above-described alkylene oxides. Similar alkylene oxide-alkanolamine reaction products can also be used such as the products made by reacting the aforedescribed primary, secondary or tertiary alkanolamines with ethylene, propylene or higher epoxides in a 1.1 to 1.2 molar ratio. Reactant ratios and temperatures for carrying out such reactions are known to those skilled in the art.

Specific examples of alkoxylated alkylenepolyamines include N-(2-hydroxyethyl)ethylenediamine, N,N-di-(2-hydroxyethyl)-ethylenediamine, 1-(2-hydroxyethyl) piperazine, mono-(hydroxypropyl)-substituted tetraethylenepentamine, N-(3-hydroxybutyl)-tetramethylene diamine, etc. Higher homologs obtained by condensation of the above illustrated hydroxy-containing polyamines through amino groups or through hydroxy groups are likewise useful. Condensation through amino groups results in a higher amine accompanied by removal of ammonia while condensation through the hydroxy groups results in products containing ether linkages accompanied by removal of water. Mixtures of two or more of any of the aforesaid polyamines are also useful.

In another embodiment, the polyamine may be a heterocyclic polyamine. The heterocyclic polyamines include aziridines, azetidines, azolidines, tetra- and dihydropyridines, pyrroles, indoles, piperidines, imidazoles, di- and tetrahydroimidazoles, piperazines, isoindoles, purines, N-aminoalkylmorpholines, N-aminoalkylthiomorpholines, N-aminoalkylpiperazines, N,N'-bisaminoalkyl piperazines, azepines, azocines, azonines, azecines and tetra-, di- and perhydro derivatives of each of the above and mixtures of two or more of these heterocyclic amines. Preferred heterocyclic amines are the saturated 5- and 6-membered heterocyclic amines containing only nitrogen, or nitrogen with oxygen and/or sulfur in the hetero ring, especially the piperidines, piperazines, thiomorpholines, morpholines, pyrrolidines, and the like. Piperidine, aminoalkylsubstituted piperidines, piperazine, aminoalkylsubstituted piperazines, morpholine, aminoalkyl-substituted morpholines, pyrrolidine, and aminoalkyl-substituted pyrrolidines, are especially preferred. Usually the aninoalkyl substituents are substituted on a nitrogen atom forming part of the hetero ring. Specific examples of such heterocyclic amines include N-aminopropylmorpholine, N-aminoethylpiperazine, and N,N'-diaminoethyl-piperazine. Hydroxy alkyl substituted heterocyclic polyamines are also useful. Examples include N-hydroxyethylpiperazine and the like.

In another embodiment, the amine is a polyalkene-substituted amine. These polyalkene-substituted amines are well known to those skilled in the art. They are disclosed in U.S. Pat. Nos. 3,275,554; 3,438,757; 3,454,555; 3,565,804; 3,755,433; and 3,822,289. These patents are hereby incorporated by reference for their disclosure of polyalkene-substituted amines and methods of making the same.

Typically, polyalkene-substituted amines are prepared by reacting halogenated-, preferably chlorinated-, olefins and olefin polymers (polyalkenes) with amines (mono- or polyamines). The amines may be any of the amines described above. Examples of these compounds include poly(propylene)amine; N,N-dimethyl-N-poly(ethylene/propylene)amine, (50:50 mole ratio of monomers); poly-butene amine; N,N-di(hydroxyethyl)-N-polybutene amine; N-(2-hydroxypropyl)-N-polybutene amine; N-polybutene-aniline; N-polybutene-morpholine; N-poly(butene) ethylenediamine; N-poly(propylene)trimethylenediamine; N-poly(butene)diethylene-triamine; N',N'-poly(butene) tetraethylene-pentamine; N,N-dimethyl-N'-poly-(propylene)-1,3-propylenediamine and the like.

The polyalkene substituted amine is characterized as containing from at least about 8 carbon atoms, preferably at least about 30, more preferably at least about 35 up to about 300 carbon atoms, preferably 200, more preferably 100. In one embodiment, the polyalkene substituted amine is characterized by an n (number average molecular weight) value of at least about 500. Generally, the polyalkene substituted amine is characterized by an n value of about 500 to about 5000, preferably about 800 to about 2500. In another embodiment n varies between about 500 to about 1200 or 1300.

The polyalkenes from which the polyalkene substituted amines are derived include homopolymers and interpolymers of polymerizable olefin monomers of 2 to about 16 carbon atoms; usually 2 to about 6, preferably 2 to about 4, more preferably 4. The olefins may be monoolefins such as ethylene, propylene, 1-butene, isobutene, and 1-octene; or a polyolefinic monomer, preferably diolefinic monomer, such 1,3-butadiene and isoprene. Preferably, the polymer is a homopolymer. An example of a preferred homopolymer is a polybutene, preferably a polybutene in which about 50% of the polymer is derived from isobutylene. The polyalkenes are prepared by conventional procedures.

It is generally preferred to utilize sufficient amine reactant (C) to convert substantially all of the intermediate arising from reaction of (A) with (B) to product; however, conversion of at least 50%, more preferably 75% is often acceptable. Preferably, at least 90%, more preferably 99–100% conversion is effected.

The reaction with the (C) reactant to prepare the products of this invention is conducted at temperatures ranging from about 25° C. to about 230° C. When the amine is an alkanolamine, an alkylene polyamine or a thioalkanol amine, N-containing heterocyclic group containing products such as imidazoline, oxazoline, or thiazoline formation may form. These are frequently obtained by first preparing an amide then continuing the reaction at elevated temperature to generate imidazoline, thiazoline or oxazoline by removal of water.

Imidazoline formation will not occur with every amine; the amine must have the structural element:

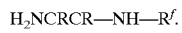

Similarly, oxazoline formation can take place when the amine is a β-hydroxyethyl amine, e.g.,

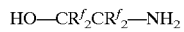

β-thiolamines can react to form thiazolines.

In the above formulae, each $R^f$ is independently H, alkoxyalkyl, hydroxyalkyl, hydrocarbyl, aminohydrocarbyl or N-alkoxyalkyl- or hydroxyalkyl-substituted amino hydrocarbyl.

Thus, if imidazoline, thiazoline or oxazoline formation is not desired, they may be avoided by employing amine reactants that do not provide the opportunity for imidazoline, thiazoline or oxazoline formation, or, if the amine employed can lead to oxazoline, thiazoline or imidazoline, to minimize formation thereof by conducting the reaction at the lowest temperature to prepare amide at an acceptable rate and in acceptable amounts, or to avoid prolonged heating of the amide-containing product, once it has formed. Infrared analysis during the reaction is a convenient means for determining the nature and extent of the reaction.

The first step of the process of this invention is conducted, usually under an inert atmosphere such as $N_2$, at temperatures ranging from ambient up to the lowest decomposition temperature of any of the reactants, usually from about 60° C. to about 220° C., more often from about 120° C. to about 180° C., preferably up to about 160° C. The process employs from more than 1.5 moles (B) per mole of (A) to 3 moles (B) per equivalent of (A), more often from about 1.8 moles (B) per mole of (A) to about 2.5 moles (B) per equivalent of (A), even more often from about 1.9 moles (B) per mole of (A) to about 2.1 moles (B) per equivalent of (A). The product formed in this first step is then reacted, at temperatures ranging from about 25° C. to about 230° C., preferably from about 60° C. to about 150° C., more often from about 100° C. to about 110° C. with (C) ammonia, a hydrazine or an amine characterized by the presence within its structure of at least one N—H group. Reactant (C) is used in amounts ranging from about 0.5 equivalents up to about 2 moles, per mole of (B).

Products obtained by post-treating the acylated nitrogen compounds of this invention are also useful. Reagents such as urea, thiourea, carbon disulfide, aldehydes, ketones, carboxylic acids, hydrocarbon substituted succinic anhydrides, nitriles, epoxides, boron compounds, phosphorus compounds and the like are useful post-treating agents.

The following examples are intended to illustrate several compositions of this invention as well as means for preparing same. Unless indicated otherwise all parts are parts by weight, filtrations are conducted employing a diatomaceous earth filter aid, and analytical values are by actual analysis. The abbreviations GPC and VPO refer to gel permeation chromatography and vapor phase osmometry, respectively, both procedures being used to determine molecular weight. The abbreviation TLC-FID refers to thin layer chromatography using a flame ionization detector. Saponification numbers are determined using ASTM Procedure D-94. Aromatic hydrocarbons are commercial aromatic hydrocarbon solvents having a flash point of about 43° C. It is to be understood that these examples are intended to illustrate several compositions and procedures of the invention and are not intended to limit the scope of the invention.

EXAMPLE 1

Part A

A reactor is charged with 250 parts of polyisobutylene (Glissopal ES3250, BASF) having $\overline{M}_n$ about 1000 and containing about 87 mole percent terminal vinylidene groups, 52 parts 50% aqueous glyoxylic acid, 15 parts paraformaldehyde and 1 part 70% aqueous methanesulfonic acid. These are heated with mixing, under $N_2$, to 160° C. and are held at temperature for a total of 4.5 hours. The materials are stripped to 135° C. and 25 millimeters Hg pressure (mm Hg) and filtered. The filtrate has saponification no=32.4, and contains (GPC) 96.3% material having $\overline{M}_n$=1432 and $\overline{M}_w$=2157.

Part B

A reactor is charged with 160 parts of the product of Part A of this example and 57.7 parts aminoethylpiperizine. The materials are mixed and heated to 160° C. over 0.5 hour under $N_2$, held for 5 hours at 160° C. while collecting 0.3 parts aqueous distillate, then the temperature is increased to 180° C. and held at temperature for a total of 10 hours. The materials are cooled and stripped to 140° C. at 20 mm Hg, collecting 26.5 parts distillate and the residue is filtered at 120° C. The filtrate contains 4.33% N, 100% $\overline{M}_n$=1530 and infrared peak at 1675 $cm_{-1}$.

EXAMPLE 2

Part A

A reactor is charged with 1200 parts of the polyisobutylene of Example 1, 177.6 parts 50% aqueous glyoxylic acid, 4.8 parts 70% aqueous methanesulfonic acid and 36 parts paraformaldehyde, the materials are reacted, under $N_2$, at 160° C. for 5.5 hours, collecting 114 parts water, cooled to 100° C., stripped to 140° C. and 20 mm Hg and filtered. The filtrate has saponification no=44 and has (VPO) $\overline{M}_n$=1852.

Part B

The reactor is charged with 200 parts of the product of Part A of this example, 136.4 parts mineral oil and 8.4 parts of an ethylenepolyamine mixture containing about 25% diethylenetriamine and the balance being heavier ethylenepolyamines and containing about 34% N. The materials are heated to 160° C. and held at 160° C. for 4 hours, collecting 2.1 parts aqueous distillate followed by 3 more hours at 160° C., cooling to 120° C. and filtration. The filtrate contains 0.86% N.

EXAMPLE 3

A reactor is charged with 200 parts of the product of Part A of Example 2, 147.9 parts mineral oil and 21.8 parts of a branched polyamine derived from the condensation of trishydroxymethylaminomethane with an ethylenepolyamine. The materials are heated with stirring under $N_2$ to 160° C., held at 160° C. for 6 hours, cooled to 135° C. and filtered. The filtrate contains 1.51% N.

EXAMPLE 4

A reactor is charged with 200 parts of the product of Part A of Example 2 and 17.1 parts of ethanolamine. The materials are heated with stirring, under $N_2$, to 160° C., held at 160° C. for 6 hours, cooled and stripped to 130° C. at 25 mm Hg and filtered. The filtrate contains 1.30% N and 0% free amine.

EXAMPLE 5

The procedure of Example 4 is repeated employing 200 parts of the product of Part A of Example 2 and 28.6 parts of dimethylaminopropylamine. The product contains 1.31% N and 0.1% free amine.

EXAMPLE 6

A reactor is charged with 200 parts of the product of Part A of Example 2 and 29.1 parts of diethylenetriamine. The materials are heated, under $N_2$, to 160° C., held at 160° C. for 4 hours and stripped to 160° C. at 25 mm Hg. The materials are cooled to 120° C., 76.4 parts aromatic diluent are added, the materials are stirred and the solution is filtered. The filtrate contains 2.06 percent N and 0% free amine.

EXAMPLE 7

Part A

Employing the same reactants as in Part A of Example 2, 3000 parts of polyisobutylene, 444 parts 50% aqueous glyoxylic acid, 12 parts 70% aqueous methanesulfonic acid and 99 parts paraformaldehyde are reacted, under $N_2$, at 160° C. for 5 hours, collecting 344 parts water then for an additional 3 hours. The materials are cooled then stripped to 160° C. and 30 mm Hg and filtered. The filtrate has saponification no=44, has (GPC) $\overline{M}_n$=1450 and contains 17% unreacted polyisobutylene.

Part B

A reactor is charged with 600 parts of the product of Part A of this Example, 40.2 parts of the branched ethylenepolyamine employed in Example 3, and 426.8 parts mineral oil. The materials are heated with stirring, under $N_2$, to 160° C. and are held for 5 hours at 160° C. The materials are cooled to 140° C. and filtered. The filtrate contains 1.0% N and has infrared absorption at 1665 $cm^{-1}$.

EXAMPLE 8

A reactor is charged with 300 parts of the product of Part A of Example 7 and 14.4 parts ethanolamine. The materials are heated to 160° C., under $N_2$, held for 5 hours at 160° C., cooled and stripped to 130° C. at 25 mm Hg. The materials are then filtered. The filtrate contains 0.6% N.

EXAMPLE 9

A reactor is charged with 300 parts of the product of Part A of Example 7 and 24 parts of N,N-dimethylaminopropylamine. The materials are heated to 160° C., under $N_2$, held for 4 hours at 160° C., cooled to 130° C., and stripped to 130° C. at 25 mm Hg. To the residue are added 108 parts aromatic diluent followed by mixing and filtration. The filtrate contains 0.85% N.

EXAMPLE 10

A reactor is charged with 300 parts of the product of Part A of Example 7, 15.4 parts of an ethylenepolyamine mixture (about 15% diethylenetriamine, 21% tetraethylenepentamine and 64% pentaethylenehexamine; 36% N) and 210.2 parts mineral oil. The materials are mixed and heated, under $N_2$, to 160° C., held for 5 hours at 160° C., cooled and filtered at 140° C. The filtrate contains 0.95% N.

EXAMPLE 11

Part A

Employing the same reactants as in Example 2, 3000 parts of polyisobutylene, 488 parts 50% aqueous glyoxylic acid, 12 parts 70% aqueous methanesulfonic acid and 99 parts paraformaldehyde are reacted, under $N_2$, at 120° C. for hours, collecting water then at 160° C. for 5 hours, collecting water. The materials are cooled to 140° C. and filtered. The filtrate has saponification no=50, has (GPC) $\overline{M}_n$=1475, $\overline{M}_w$=2422 and contains 15% unreacted polyisobutylene.

Part B

A reactor is charged with 26.8 parts of the branched ethylenepolyamine of Example 3 and 251.2 parts mineral oil. The materials are mixed and heated, under $N_2$, to 155° C. whereupon 350 parts of the product of Part A of this example are added dropwise over 0.75 hours while maintaining the temperature between 155°–160° C. The materials are reacted at 160° C. for 5 hours, cooled to 135° C. and filtered. The filtrate contains 1.1% N and 158 ppm chlorine.

EXAMPLE 12

The process of Example 10 is repeated employing 350 parts of the product of Part A of Example 11, 247 parts mineral oil and 20.5 parts of amine. The product contains 1.12% N and 0% chlorine.

EXAMPLE 13

A reactor is charged with 250 parts of the product of Part A of Example 11 and 174.1 parts mineral oil diluent. The materials are heated, under $N_2$, to 160° C. To this solution, dropwise over 7 hours, is added 116.7 parts 30% aqueous ammonia while holding the temperature at 160° C. and collecting water in a Dean-Stark trap. The materials are heated at 160° C. for 4 hours, stripped to 160° C. at 40 mm Hg, cooled to 140° C. and filtered. The filtrate contains 0.17% N.

EXAMPLE 14

A reactor is charged with 250 parts of the product of Part A of Example 11 and 169 parts mineral oil. The materials are heated, under $N_2$, to 160° C., whereupon 79 parts 40% aqueous methylamine are added over 7 hours while maintaining the temperature at 160° C. and collecting aqueous distillate. The materials are heated at 160° C. for 4 hours, stripped to 160° C. at 25 mm Hg, cooled to 140° C. and filtered. The product contains 0.34% N.

EXAMPLE 15

A reactor is charged with 350 parts of the product of Part A of Example 11, 247.3 parts mineral oil and 20.97 parts of ethylenepolyamine bottoms having an equivalent weight of 40.5 per N (HPA-X, Union Carbide). The materials are heated to 160° C., under $N_2$, held for 5 hours at 160° C., cooled to 145° C. and filtered. The product contains 1.08% N and 0% chlorine.

EXAMPLE 16

Part A

A reactor is charged with 832 parts of polyisobutylene (Glissopal ES3252) having $\overline{M}_n$ about 240 and containing about 70 mole percent terminal vinylidene groups, 61.6 parts 50% aqueous glyoxylic acid, 13.7 parts paraformaldehyde, 3 parts 70% aqueous methanesulfonic acid, and 571.2 parts mineral oil. The materials are heated to 120° C. over 1 hour, collecting water, then to 160° C. over 1 hour, reacted at 160° C. for 8 hours, while collecting water. The materials are stripped to 160° C. and 25 mm Hg and filtered at 140° C. The filtrate has saponification no=13.4. (GPC) $\overline{M}_n$=4324, $\overline{M}_w$=9779 (65%) and $\overline{M}_n$=340, $\overline{M}_w$=412. (35%).

Part B

A reactor is charged with 600 parts of the product of Part A of this example, 6 parts mineral oil and 9 parts of the polyamine bottoms of Example 15. The materials are heated, under $N_2$, to 160° C. and held at temperature for 5 hours. The materials are filtered. The product contains 0.56% N and 0% chlorine.

EXAMPLE 17

Part A

A reactor is charged with 4000 parts polyisobutylene (Ultravis 10, BP Chemicals) having $\overline{M}_n$ about 1000 and containing about 80 mole % terminal vinylidene groups, 592 parts 50% aqueous glyoxylic acid, 132 parts paraformaldehyde and 16 parts 70% aqueous methanesulfonic acid. The materials are heated to 120° C. over 0.75 hour then to 160° C. over 2.5 hours, collecting water, then reacted at 160° C. for a total of 6 hours; total water collected, 475 parts. The materials are stripped to 160° C. and 40 mm Hg and filtered. The filtrate contains 19.9% unreacted polyisobutylene, has saponification no.=42 and (GPC) $\overline{M}_n$=1419, $\overline{M}_w$=3272.

Part B

A reactor is charged with 200 parts of the product of Part A of this example, and 11.55 parts diethylenetriamine. The materials are heated, under $N_2$, to 160° C. and held at temperature for 5 hours followed by stripping to 160° C. at 25 mm Hg. The materials are cooled to 130° C., 70.6 parts aromatic diluent are added, the materials are mixed and filtered. The filtrate contains 1.6% N and shows infrared absorption at 1670 $cm^{-1}$.

EXAMPLE 18

The procedure of Example 17B is followed except the reaction temperature is 180° C. The product contains 1.37% N and has infrared absorption at 1665 $cm^{-1}$.

EXAMPLE 19

A reactor is charged with 200 parts of the product of Part A of Example 17 and 9.65 parts aminoethylpiperizine. The materials are heated, under $N_2$, to 180° C. and held at temperature for 5 hours. The materials are stripped to 180° C. at 40 mm Hg, cooled to 130° C. whereupon 69.9 parts aromatic diluent are added, the materials are mixed and filtered. The product contains 1.13% N and has infrared absorption at 1675 $cm^{-1}$.

EXAMPLE 20

The procedure of Example 19 is repeated except the reaction is conducted at 160° C. The product contains 1.13% N and has infrared absorption at 1675 $cm^{-1}$.

EXAMPLE 21

The procedure of Example 19 is repeated employing 14.5 parts aminoethylpiperizine and 71.5 parts aromatic diluent. The product contains 1.52% N and has infrared absorption at 1675 $cm^{-1}$.

EXAMPLE 22

The procedure of Example 20 is repeated employing 14.4 parts aminoethylpiperizine and 71.5 parts aromatic diluent. The product contains 1.59% N and has infrared absorption at 1675 $cm^{-1}$.

EXAMPLE 23

A reactor is charged with 200 parts of the product of Part A of Example 17, and 19.3 parts aminoethylpiperizine. The materials are heated to 200° C., under $N_2$, and held at temperature for 5 hours. The materials are stripped to 200° C. at 25 mm Hg, cooled to 130° C. whereupon 73.1 parts aromatic diluent are added. The materials are filtered. The filtrate contains 1.62% N and has infrared absorption at 1675 cm$^{-1}$.

EXAMPLE 24

The procedure of Example 23 is repeated except the reaction is conducted at 180° C. The product contains 1.91% N and has infrared absorption at 1675 cm$^{-1}$.

EXAMPLE 25

The procedure of Example 23 is repeated except the reaction is conducted at 160° C. The product contains 2% N.

EXAMPLE 26

The procedure of Example 2 is repeated replacing the glyoxylic acid with an equivalent amount of pyruvic acid.

EXAMPLE 27

The procedure of Example 4 is repeated replacing glyoxylic acid with an equivalent amount of levulinic acid.

EXAMPLE 28

The procedure of Example 1 is repeated replacing glyoxylic acid with an equivalent amount of glyoxylic acid methyl ester methyl hemiacetal.

EXAMPLE 29

The procedure of Example 4 is repeated replacing glyoxylic acid with an equivalent amount of glyoxylic acid methyl ester methyl hemiacetal.

EXAMPLE 30

Part A

A reactor is charged with 1000 parts of the polyisobutylene used in Example 1, 148 parts of 50% aqueous glyoxylic acid, 29 parts glyoxal and 2 parts 70% aqueous methane sulfonic acid. Under $N_2$, the materials are heated to 130° C., held at 130° C. for 2 hours, heated to 160° C., and held at 160° C. for 4 hours, while collecting a total of 108 parts aqueous distillate. The materials are mixed with 730.7 parts mineral oil and filtered at 140° C. obtaining a filtrate having total acid no=11.8 and saponification no=26.5.

Part B

A reactor is charged with 300 parts of the product of Part A of this example, 13.7 parts of a branched polyamine derived from the condensation of tris-hydroxymethylaminomethane with an ethylenepolyamine, and 9.1 parts mineral oil. The materials are heated to 160° C. and maintained at temperature for 5 hours. The materials are cooled to 140° C. and filtered. The filtrate contains 1.08% N and has infrared absorption at 1665 cm$^{-1}$.

EXAMPLE 31

Part A

A reactor is charged with 800 parts of the polyisobutylene used in Example 1, 118.4 parts of 50% aqueous glyoxylic acid, 18.6 parts glyoxal and 1.6 parts 70% aqueous methane sulfonic acid. Under $N_2$, the materials are heated to 140° C., held at 140°–148° C. for 6 hours, then at 145° C. for 7 hours, collecting aqueous distillate. The materials are mixed with 567 parts mineral oil and filtered at 145° C. obtaining a filtrate having total acid no=0, saponification no=23.2 and (GPC) 59.94% $\overline{M}_n$=1743, $\overline{M}_w$=2184; 40.1% $\overline{M}_n$=358.

Part B A reactor is charged with 300 parts of the product of Part A of this example, 13.7 parts of the branched polyamine used in Example 30 and 22.8 parts mineral oil. The materials are heated to 160° C. and held at temperature for 6 hours. The materials are filtered at 145° C. The filtrate contains 1.05% N and has infrared absorption at 1660 cm$^{-1}$.

EXAMPLE 32

A reactor is charged with 300 parts of the product of Example 31 Part A, 7.84 parts of the amine used in Example 10 and 5.24 parts mineral oil. The materials are heated to 160° C., held at 160° C. for 5 hours, cooled to 145° C. and filtered. The filtrate contains 0.83% N and has infrared absorption at 1665 cm$^{-1}$.

EXAMPLE 33

The procedure of Example 32 is repeated replacing the amine of Example 10 with the amine bottoms of Example 15. The product contains 0.79% N and has infrared absorption at 1665 cm$^{-1}$.

EXAMPLE 34

Part A

A reactor is charged with 1000 parts of the polyisobutylene used in Example 1, 37 parts 50% aqueous glyoxylic acid, 35.6 parts nonyl aldehyde and 1 part 70% aqueous methane sulfonic acid. The materials are heated, under $N_2$, to 160° C. and are held at 160° C. for 5 hours while collecting 23.9 parts aqueous distillate. The materials are stripped to 125° C. at 56 mm Hg, then filtered at 120° C. The filtrate has total acid no.=14.8, saponification no.=36.4 and, by GPC, 100% $\overline{M}_n$=1191, $\overline{M}_w$=1881, and contains 25% unreacted polyisobutylene (TLC-FID).

Part B

A reactor is charged with 200 parts of the product of Part A of this Example and 30 parts of dimethylaminopropylamine, reacted for 4 hours at 160° C., stripped to 160° C. at 25 mm Hg and filtered.

EXAMPLE 35

The process of Part A of Example 1 is repeated employing 0.1 mole % $AlCl_3$ catalyst, filtered by the process of Part B.

EXAMPLE 36

The process of Part A of Example 1 is repeated employing 0.1 mole % $FeCl_3$ catalyst, followed by the process of Part B.

EXAMPLE 37

The process of Part A of Example 1 is repeated employing 0.2 mole % $BF_3$ catalyst, followed by the process of Part B.

EXAMPLE 38

The process of Example 1 is repeated replacing glyoxylic acid with an equal molar amount of pyruvic acid.

EXAMPLE 39

The process of Example 1 is repeated replacing glyoxylic acid with an equal molar amount of levulinic acid.

EXAMPLE 40

The product of Example 1, Part B is post treated with 1% by weight $H_3BO_3$ at 130° C., removing aqueous distillate as it forms.

The Lubricating Oil Compositions
The Oil of Lubricating Viscosity

In one embodiment of this invention, the compositions are lubricating oil compositions. The lubricating compositions employ an oil of lubricating viscosity, including natural or synthetic lubricating oils and mixtures thereof. Mixtures of mineral oil and synthetic oils, particularly polyalphaolefin oils and polyester oils, are often used. The lubricating composition of this invention comprise a major amount of an oil of lubricating viscosity and a minor amount of the composition of this invention.

By major amount is meant greater than 50% by weight, while minor amount means less than 50% by weight, based on the total weight of the composition.

Natural oils include animal oils and vegetable oils (e.g. castor oil, lard oil and other vegetable acid esters) as well as mineral lubricating oils such as liquid petroleum oils and solvent-treated or acid treated mineral lubricating oils of the paraffinic, naphthenic or mixed paraffinic-naphthenic types. Hydrotreated or hydrocracked oils are included within the scope of useful oils of lubricating viscosity.

Oils of lubricating viscosity derived from coal or shale are also useful. Synthetic lubricating oils include hydrocarbon oils and halosubstituted hydrocarbon oils such as polymerized and interpolymerized olefins, etc. and mixtures thereof, alkylbenzenes, polyphenyl, (e.g., biphenyls, terphenyls, alkylated polyphenyls, etc.), alkylated diphenyl ethers and alkylated diphenyl sulfides and their derivatives, analogs and homologues thereof and the like.

Alkylene oxide polymers and interpolymers and derivatives thereof, and those where terminal hydroxyl groups have been modified by esterification, etherification, etc., constitute other classes of known synthetic lubricating oils that can be used.

Another suitable class of synthetic lubricating oils that can be used comprises the esters of dicarboxylic acids and those made from $C_5$ to $C_{12}$ monocarboxylic acids and polyols or polyol ethers.

Other synthetic lubricating oils include liquid esters of phosphorus-containing acids, polymeric tetrahydrofurans and the like, silicon-based oils such as the polyalkyl-, polyaryl-, polyalkoxy-, or polyaryloxy-siloxane oils and silicate oils.

Hydrotreated naphthenic oils are well known.

Unrefined, refined and rerefined oils, either natural or synthetic (as well as mixtures of two or more of any of these) of the type disclosed hereinabove can used in the compositions of the present invention. Unrefined oils are those obtained directly from a natural or synthetic source without further purification treatment. Refined oils are similar to the unrefined oils except they have been further treated in one or more purification steps to improve one or more properties. Rerefined oils are obtained by processes similar to those used to obtain refined oils applied to refined oils which have been already used in service. Such rerefined oils often are additionally processed by techniques directed to removal of spent additives and oil breakdown products.

Specific examples of the above-described oils of lubricating viscosity are given in Chamberlin III, U.S. Pat. No. 4,326,972 and European Patent Publication 107,282, both of which are hereby incorporated by reference for relevant disclosures contained therein.

A basic, brief description of lubricant base oils appears in an article by D. V. Brock, "Lubrication Engineering", Volume 43, pages 184–5, March, 1987, which article is expressly incorporated by reference for relevant disclosures contained therein.

Other Additives

The lubricating oil compositions of this invention may contain minor amounts of other components. The use of such components is optional and the presence thereof in the compositions of this invention will depend on the particular use and level of performance required. Thus these components may be included or excluded.

The compositions may comprise a zinc salt of a dithiophosphoric acid. Zinc salts of dithiophosphoric acids are often referred to as zinc dithiophosphates, zinc O,O-dihydrocarbyl dithiophosphates, and other commonly used names. They are sometimes referred to by the abbreviation ZDP. One or more zinc salts of dithiophosphoric acids may be present in a minor amount to provide additional extreme pressure, anti-wear and anti-oxidancy performance.

In addition to zinc salts of dithiophosphoric acids discussed hereinabove, other additives that may optionally be used in the lubricating oils of this invention include, for example, detergents, dispersants, viscosity improvers, oxidation inhibiting agents, metal passivating agents, pour point depressing agents, extreme pressure agents, anti-wear agents, color stabilizers and anti-foam agents. The above-mentioned dispersants and viscosity improvers are used in addition to the additives of this invention.

Auxiliary extreme pressure agents and corrosion and oxidation inhibiting agents which may be included in the compositions of the invention are exemplified by chlorinated aliphatic hydrocarbons, organic sulfides and polysulfides, phosphorus esters including dihydrocarbon and trihydrocarbon phosphites, molybdenum compounds, and the like.

Viscosity improvers (also sometimes referred to as viscosity index improvers) may be included in the compositions of this invention. Viscosity improvers are usually polymers, including polyisobutenes, polymethacrylic acid esters, diene polymers, polyalkyl styrenes, alkenylarene-conjugated diene copolymers and polyolefins. Multifunctional viscosity improvers, other than those of the present invention, which also have dispersant and/or antioxidancy properties are known and may optionally be used in addition to the products of this invention. Such products are described in numerous publications including those mentioned in the Background of the Invention. Each of these publications is hereby expressly incorporated by reference.

Pour point depressants are a particularly useful type of additive often included in the lubricating oils described herein. See for example, page 8 of "Lubricant Additives" by C. V. Smalheer and R. Kennedy Smith (Lezius-Hiles Company Publisher, Cleveland, Ohio, 1967). Pour point depressants useful for the purpose of this invention, techniques for their preparation and their use are described in U.S. Pat. Nos. 2,387,501; 2,015,748; 2,655,479; 1,815,022; 2,191,498; 2,666,748; 2,721,877; 2,721,878; and 3,250,715 which are expressly incorporated by reference for their relevant disclosures.

Anti-foam agents used to reduce or prevent the formation of stable foam include silicones or organic polymers. Examples of these and additional anti-foam compositions are described in "Foam Control Agents", by Henry T. Kerner (Noyes Data Corporation, 1976), pages 125–162.

Detergents and dispersants may be of the ash-producing or ashless type. The ash-producing detergents are exemplified by oil soluble neutral and basic salts of alkali or alkaline earth metals with sulfonic acids, carboxylic acids, phenols or organic phosphorus acids characterized by at least one direct carbon-to-phosphorus linkage.

The term "basic salt" is used to designate metal salts wherein the metal is present in stoichiometrically larger amounts than the organic acid radical. Basic salts and techniques for preparing and using them are well known to those skilled in the art and need not be discussed in detail here.

Ashless detergents and dispersants are so-called despite the fact that, depending on its constitution, the detergent or dispersant may upon combustion yield a nonvolatile residue such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in British Patent number 1,306,529 and in any U.S. Pat. Nos. including the following:

| | | |
|---|---|---|
| 3,163,603 | 3,381,022 | 3,542,680 |
| 3,184,474 | 3,399,141 | 3,567,637 |
| 3,215,707 | 3,415,750 | 3,574,101 |
| 3,219,666 | 3,433,744 | 3,576,743 |
| 3,271,310 | 3,444,170 | 3,630,904 |
| 3,272,746 | 3,448,048 | 3,632,510 |
| 3,281,357 | 3,448,049 | 3,632,511 |
| 3,306,908 | 3,451,933 | 3,697,428 |
| 3,311,558 | 3,454,607 | 3,725,441 |
| 3,316,177 | 3,467,668 | 4,194,886 |
| 3,340,281 | 3,501,405 | 4,234,435 |
| 3,341,542 | 3,522,179 | 4,491,527 |
| 3,346,493 | 3,541,012 | RE 26,433 |
| 3,351,552 | 3,541,678 | |

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.:

| | |
|---|---|
| 3,275,554 | 3,454,555 |
| 3,438,757 | 3,565,804 |

(3) Reaction products of alkyl phenols in which the alkyl groups contains at least about 30 carbon atoms with aldehydes (especially formaldehyde) and amines (especially polyalkylene polyamines), which may be characterized as "Mannich dispersants". The materials described in the following U.S. Pat. Nos. are illustrative:

| | |
|---|---|
| 3,413,347 | 3,725,480 |
| 3,697,574 | 3,726,882 |
| 3,725,277 | |

(4) Products obtained by post-treating the carboxylic amine or Mannich dispersants with such reagents are urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |
| | | | 4,234,435 |

(5) Interpolymers of oil-solubilizing monomers such as decyl methacrylate, vinyl decyl ether and high molecular weight olefins with monomers containing polar substituents, e.g., aminoalkyl acrylates or methacrylates, acrylamides and poly-(oxyethylene)-substituted acrylates. These may be characterized as "polymeric dispersants" and examples thereof are disclosed in the following U.S. Pat. Nos.:

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

The above-illustrated additives may each be present in lubricating compositions at a concentration of as little as 0.001% by weight usually ranging from about 0.01% to about 20% by weight, more often from about 1% to about 12% by weight.

The compositions of the present invention are present in a minor amounts, often amounts ranging from about 1% to about 20% by weight, more often from about 3% to about 10% by weight, even more often from about 5% to about 8% by weight.

Additive Concentrates

The various additives described herein can be added directly to the lubricating oil or fuel. Preferably, however, they are diluted with a substantially inert, normally liquid organic diluent such as mineral oil, naphtha, benzene, toluene or xylene, to form an additive concentrate. These concentrates usuallycomprise about 0.1 to about 80% by weight, frequently from about 1% to about 80% by weight, more often from about 10% to about 80% by weight, of the compositions of this invention and may contain, in addition, one or more other additives known in the art or described hereinabove. The balance comprises the normally liquid organic diluent. Concentrations such as 15%, 20%, 30% or 50% or higher may be employed.

Additive concentrates are prepared by mixing together, often at elevated temperature, the desired components.

Additive concentrates used for preparing lubricating oil compositions are illustrated by the following examples. The amounts shown are indicated as parts by weight or parts by volume. Unless indicated otherwise, components are indicated as parts or percentages by weight of chemical present on an oil or diluent free basis. When products of Examples set forth hereinabove are used, the amounts listed are as prepared, including diluent, if any. The abbreviation MR refers to metal ratio, the relative amount of metal in an overbased salt compared to the amount expected based on stoichiometry. For example, MR=2 means the overbased material contains twice the amount of metal compared to the "normal" stoichiometric amount.

Additive concentrates are prepared by blending the components listed in the following Tables. Mineral oil is used to bring the total to 100 parts.

TABLE 1

7.03 parts Ca overbased (MR ~ 1.1) S-coupled alkyl phenate, 4.84 parts Ca overbased (MR ~ 3.5) S-coupled alkyl phenate, 1.97 parts di-(nonyl phenyl) amine, 3.9 parts Ca overbased (Mr ~ 1.2) alkyl benzene sulfonate, 3.19 parts Mg overbased (MR 14.7) alkyl benzene sulfonate, 0.01 parts silicone antifoam, 9.14 parts zinc salt of di-mixed isopropyl-isoctyl dithiophosphate, 9.02 parts polybutene ($M_n$ ~ 1000) substituted succinic anhydride-pentaerythritol/alkylene amine reaction product and the indicated amounts of the products of listed Examples:

Example (Parts by Weight)

| Product of Example | A | B | C | D | E | F | G |
|---|---|---|---|---|---|---|---|
| 11B | 34.38 | | | | 47.83 | | |
| 12 | | 34.38 | | | | 47.83 | |
| 15 | | | 34.38 | | | | 47.83 |
| 16B | | | | 34.84 | | | |

TABLE 2

ADDITIVE CONCENTRATES 5.65 parts t-Butyl-propylene tetramer substituted phenol, 9.39 parts zinc salt of di-mixed isopropyl-methyl amyl dithiophosphate, 5.22 parts sulfurized (26% S) butadiene-butyl acrylate Diels-Alder adduct, 2.19 parts di(nonyl phenyl) amine, 0.87 parts sunflower oil, 6.12 parts Na overbased (MR ~ 15) polybutene $M_n$ ~ 1000) substituted succinic acid, 1.48 parts Mg overbased (MR ~ 14.7) alkyl benzene sulfonate, 0.01 parts silicone antifoam, and the indicated amounts of the products of the listed Examples:

| Component: (parts by weight) | Example: H | I | J |
|---|---|---|---|
| Borated rctn product of polybutene ($M_n$ ~ 1000) subst. succinic anhydride and ethylene polyamine | 2.8 | 2.8 | |
| Dibutyl phosphite | 0.83 | 0.83 | 2.34 |
| Styrene-maleate copolymer neutralized with aminopropyl morpholine | 15.46 | 15.46 | 13.62 |
| Hydrorefined mineral oil | 8.33 | 8.33 | 22.0 |
| Di(nonyl phenyl) amine | 1.75 | 1.75 | 6.2 |
| Dithiocarbamate from dibutyl dithiocarbamic acid and methyl acrylate | 4.2 | 4.2 | |
| Mercaptan-propylene oxide reaction product | 6.3 | 6.3 | |
| Product of Example 11B | 29.2 | | |
| Product of Example 12 | | 29.2 | |
| Product of Example 7B | | | 29.4 |

The lubricating compositions of this invention are illustrated in the following Examples. The lubricating compositions are prepared by combining the specified ingredients, individually or from concentrates, in the indicated amounts and oil of lubricating viscosity to make the total 100 parts by weight. The amounts shown are indicated as parts by weight. Unless indicated otherwise, where components are indicated as parts by weight, they are amounts of chemical present on an oil or diluent free basis. Thus, for example, an additive comprising 50% oil used at 10% by weight in a blend, provides 5% by weight of chemical. Totals are 100% by weight or 100 parts by weight. However, when referring to incorporation of products of Examples set forth herein, amounts are as prepared, including any diluent.

EXAMPLES I–IV

Lubricating oil compositions are prepared by mixing together in a mineral oil of lubricating viscosity (Exxon 15W40), 7.5 parts of a 91% oil solution of an ethylene-propylene-diene copolymer and the indicated amount of the additive concentrates set forth in the following table:

| Additive Concentrate/Parts by Weight | |
|---|---|
| Example | |
| I | Example A/12.8 |
| II | Example B/12.8 |
| III | Example C/12.8 |
| IV | Example D/13.3 |

EXAMPLE V–VII

Lubricating oil compositions are prepared by mixing together a mineral oil of lubricating viscosity (5W-30), 1% of a styrene-diene copolymer viscosity improver and 0.08% of a styrene-maleate copolymer neutralized with aminopropyl morpholine and 11.5% of the indicated additive concentrate.

| Example | V | VI | VII |
|---|---|---|---|
| Product of Example | E | F | G |

EXAMPLE VIII–IX

An automatic transmission fluid is prepared by mixing together in a mineral oil of lubricating viscosity, (Exxon ATF Base, 85N), 0.025% of a red dye, 0.01% of a mixture of silicone antifoam agents and 12% of the indicated additive concentrate:

| Example | VIII | IX |
|---|---|---|
| Product of Example | H | I |

EXAMPLE X

An automatic transmission fluid as in Example VIII wherein 13.2% of the additive concentrate of Example J replaces that of Example H.

The Fuel Compositions

The Normally Liquid Fuels

As indicated hereinabove, the products of this invention may also be used as additives for normally liquid fuels.

Fuel compositions of this invention comprise a major amount of a normally liquid fuel, i.e., one which is liquid under normal conditions of use, typically, at ambient temperature, and minor amounts of the compositions of this invention, where major amount and minor amount are as defined hereinabove.

The fuels used in the fuel compositions of this invention are well known to those skilled in the art and usually contain a major portion of a normally liquid fuel such as hydrocarbonaceous petroleum distillate fuel (e.g., motor gasoline as defined by ASTM Specifications D439-89 and D4814-91 and diesel fuel or fuel oil as defined in ASTM Specifications D-396-90 and D-975-91). Fuels containing non-hydrocarbonaceous materials such a alcohols, ether, organo-nitro compounds and the like (e.g., methanol, ethanol, diethyl ether, methyl ethyl ether, nitromethane) are also within the scope of this invention as are liquid fuels derived from vegetable or mineral sources. Vegetable or mineral sources include, for example, crude petroleum oil, coal, corn, shale, oilseeds and other sources.

Oxygenates are compounds covering a range of alcohol and ether type base fuel. They have also been used as the sole fuel component, but more often as a supplemental fuel used together with, for example, gasoline to form the well-known "gasohol" blend fuels. Oxygenate-containing fuels are described in ASTM D4814-91.

Methanol and ethanol are commonly used oxygenates. They are primarily used as fuels. Other oxygenates, such as ethers, for example methyl-t-butyl ether, are more often used as octane number enhancers for gasoline.

Mixtures of fuels are useful. Examples of fuel mixtures are combinations of gasoline and ethanol, diesel fuel and ether, gasoline and nitromethane, etc.

Particularly preferred fuels are gasoline, that is, a mixture of hydrocarbons having an ASTM boiling point of 60° C. at the 10% distillation point to about 205° C. at the 90% distillation point, oxygenates, and gasoline-oxygenate blends, all as defined in the aforementioned ASTM Specifications for automotive gasolines. Most preferred is gasoline.

The fuel compositions of the present invention may contain other additives which are well known to those of skill in the art. These can include anti-knock agents such as tetra-alkyl lead compounds, lead scavengers such as haloalkanes, dyes, antioxidants such as hindered phenols, rust inhibitors such as alkylated succinic acids and anhydrides and derivatives thereof, bacteriostatic agents, auxiliary dispersants and detergents, gum inhibitors, fluidizers, metal deactivators, demulsifiers, anti-icing agents and the like. The fuel compositions of this invention may be lead-containing or lead-free fuels. Preferred are lead-free fuels.

The products of this invention provide a number of benefits to a treated fuel, including detergency, anticorrosion and the like.

In one particular embodiment of this invention, the motor fuel compositions contain an amount of additives sufficient to provide total intake system cleanliness. In another embodiment, they are used in amounts sufficient to prevent or reduce the formation of intake valve deposits or to remove them where they have formed.

As mentioned hereinabove, fluidizers may be used in the fuel compositions of the instant invention. Useful fluidizers include natural oils or synthetic oils, or mixtures thereof. Natural oils include mineral oils, vegetable oils, animal oils, and oils derived from coal or shale. Synthetic oils include hydrocarbon oils such as alkylated aromatic oils, olefin oligomers, esters, including esters of polycarboxylic acids, polyols, polyethers, poly(oxyalkylene) glycols, alkylphenol-derived polyethers, and others.

Fluidizers are usually fuel soluble, meaning they are soluble in the fuel in amounts of at least 0.1% by weight, more preferably at least 1% by weight. Certain fluidizers, for example, butylene- and propylene oxide derived fluidizers, are generally soluble in fuels at all levels. These are readily prepared from alcohol, glycol and phenol initiators under superatmospheric conditions, preferably in the presence of basic catalysts.

Especially preferred mineral oils are paraffinic oils containing no more than about 20% unsaturation, that is, no more than 20% of the carbon to carbon bonds are olefinic.

Specific examples of synthetic oil fluidizers are polyoxyalkylene mono- and polyols, ether derivatives thereof and N-vinylpyrrolidinone addition products thereof, polyalphaolefins, and hydrogenated polyalphaolefins.

Particularly useful synthetic oils are the polyether oils such as those marketed under the UCON tradename by Union Carbide Corporation, poly(oxyalkylene) glycols such as those marketed under the EMKAROX tradename by ICI Chemicals and described in EP 0647700-A1 based on U.S. Ser. No. 133,442 filed Oct. 6, 1993 and polyester oils derived from a polyol and one or more monocarboxylic acids such as those marketed by Hatco Corporation.

Other examples are polyoxyalkylene compounds prepared from $C_{1-30}$ alcohols or $C_{7-24}$ alkylphenols and sufficient propylene- or butylene oxide such that molecular weight ranges from about 200 to about 5,000, and monoethers and N-vinylpyrrolidinone addition products thereof. Additional fluidizers include polyoxyalkylene compounds prepared from glycols or polyols having from 2 to about 10 carbon atoms and sufficient propylene- or butylene oxide such that overall molecular weight ranges from about 200 to about 6,000 and ether derivatives thereof.

Preferably, the fluidizers have a kinematic viscosity ranging from about 2 to about 25 centistokes at 100° C., preferably from about 4 to about 20 centistokes, and often up to about 15 centistokes. If the viscosity of the fluidizer is too high, a problem that may arise is the development of octane requirement increase (ORI) wherein the octane value demands of the engine tend to increase with time of operation.

While both mineral oils and synthetic oils are generally useful as fluidizers over the entire preferred viscosity range, it has been observed that at the lower end of the viscosity range, synthetic oils tend to provide somewhat superior performance compared to mineral oils.

It has been found that fluidizers, particularly when used within the ranges specified herein, together with the compositions of this invention, improve detergency and emissions, and reduce the tendency toward valve sticking. Amounts of the various additives, including individual amounts to be used in the fuel composition, and relative amounts of additives are given hereinafter.

The fuel compositions of this invention may contain auxiliary dispersants. A wide variety of dispersants are known in the art and may be used together with the amide compounds described herein. Preferred auxiliary dispersants are Mannich type dispersants, acylated nitrogen-containing dispersants, aminophenol dispersants, aminocarbamate dispersants, ester dispersants and amine dispersants.

Acylated nitrogen-containing compounds include reaction products of hydrocarbyl-substituted carboxylic acylating agents such as substituted carboxylic acids or derivatives thereof with ammonia or amines. Especially preferred are succinimide dispersants.

Acylated nitrogen-containing compounds are known in the art and are disclosed in, for example, U.S. Pat. Nos. 4,234,435; 3,215,707; 3,219,666; 3,231,587 and 3,172,892, which are hereby incorporated by reference for their disclosures of the compounds and the methods of preparation.

The auxiliary dispersant may also be an ester. These compounds are prepared by reacting a hydrocarbyl-substituted carboxylic acylating agent with at least one organic hydroxy compound. In another embodiment, the ester dispersant is prepared by reacting the acylating agent with a hydroxyamine. Preferred are succinic esters.

Carboxylic esters and methods of making the same are known in the art and are disclosed in U.S. Pat. Nos. 3,219,666, 3,381,022, 3,522,179 and 4,234,435 which are hereby incorporated by reference for their disclosures of the preparation of carboxylic ester dispersants.

The carboxylic esters may be further reacted with at least one amine and preferably at least one polyamine. These nitrogen-containing carboxylic ester dispersant compositions are known in the art, and the preparation of a number of these derivatives is described in, for example, U.S. Pat. Nos. 3,957,854 and 4,234,435 which have been incorporated by reference previously.

Also included among the auxiliary dispersants are Mannich type dispersants. Mannich products are formed by the reaction of at least one aldehyde, at least one amine having at least one N—H group and at least one hydroxyaromatic compound.

Mannich products are described in the following patents: U.S. Pat. No. 3,980,569; U.S. Pat. No. 3,877,899; and U.S. Pat. No. 4,454,059 (herein incorporated by reference for their disclosure to Mannich products).

The auxiliary dispersant may be a polyalkene-substituted amine. Polyalkene-substituted amines are well known to those skilled in the art. Typically, polyalkene-substituted amines are prepared by reacting olefins and olefin polymers (polyalkenes) and halogenated derivatives thereof with amines (mono- or polyamines). These amines are disclosed in U.S. Pat. Nos. 3,275,554; 3,438,757; 3,454,555; 3,565,804; 3,755,433; and 3,822,289. These patents are hereby incorporated by reference for their disclosure of hydrocarbyl amines and methods of making the same.

Aminophenols are also included among useful auxiliary dispersants that may be used in the fuel composition of this invention. Typically, such materials are prepared by reducing hydrocarbyl substituted nitrophenols to the corresponding aminophenol. Useful aminophenols include those described in Lange, U.S. Pat. Nos. 4,320,000 and 4,320,021. Aminophenols and methods for preparing are described in U.S. Pat. Nos. 4,100,082 and 4,200,545 to Clason et al, U.S. Pat. No. 4,379,065 (Lange) and U.S. Pat. No. 4,425,138 (Davis). It should be noted that the term "phenol" used in the context of aminophenols is not intended to limit the compounds referred to in that manner as being only hydroxybenzene derivatives. The term "phenol" is intended to encompass hydroxy aromatic compounds, including hydroxybenzene compounds, naphthols, catechols and others as described in the foregoing patents, all of which are incorporated herein by reference for relevant disclosures contained therein.

Also included among useful auxiliary dispersants are aminocarbamate dispersants such as those described in U.S. Pat. No. 4,288,612, which is incorporated herein by reference for relevant disclosures contained therein.

Treating levels of the additives used in this invention are often described in terms of pounds of additive per thousand barrels (PTB) of fuel. PTB values may be converted to approximate values expressed as parts (by weight) per million parts (by weight) of fuel by multiplying PTB by 4 for gasoline and by 3.3 for diesel oil and fuel oil. To determine precise values it is necessary that the specific gravity of the fuel is known. The skilled person can readily perform the necessary mathematical calculations.

The fuel compositions of this invention contain from about 5 to about 500 pounds per thousand barrels (PTB) of fuel additive, preferably from about 10 to about 250 PTB, more preferably from about 20 to about 100 PTB.

Fluidizers, when used, are generally present in amounts ranging from about 1 to about 500 PTB, more often from about 10 to about 250 PTB and most preferably from about 10 to about 150 PTB.

Relative amounts by weight, of the nitrogen-containing compound to fluidizer oil typically range from about 1:0 that is, essentially free of fluidizer, up to 1:10, more often from about 1:0.5–2:0, preferably from about 1:0.75–1.25.

Additive Concentrates

As mentioned hereinabove, the additives for use in fuels may be supplied as additive concentrates which are then diluted with normally liquid fuels.

The following Table illustrates additive concentrates for use in fuels.

|  | Concentrate (% by Weight) | | |
| --- | --- | --- | --- |
| Component | F-I | F-II | F-III |
| Alkylated aromatic hydrocarbon[1] | 15.76 | 19.2 | 50 |
| Product of Example 4 |  |  | 23.5 |
| Product of Example 9 | 33.38 | 38 |  |
| Demulsifiers | 0.22 |  |  |
| Polyether Oil[2] |  | 42.8 |  |
| Mineral oil | 45.94 |  | 26.5 |
| 2-Ethylhexanol | 4.54 |  |  |

[1]= HISOL-10, Ashland Chemical Co.
[2]= EMKAROX AF-20, ICI

The following examples illustrate several fuel compositions of this invention. When referring to compounds described in the Examples, amounts are given in parts and percentages by weight as prepared. Unless indicated otherwise, all other parts and percentages are by weight and amounts of additives are expressed in amounts substantially free of mineral oil or hydrocarbon solvent diluent. The abbreviation 'PTB' means pounds of additive per thousand barrels of fuel.

The following Tables illustrate several fuel compositions of the instant invention comprising unleaded gasoline and the indicated amounts of additive in percent by weight concentrate in fuel.

| UNLEADED GASOLINE + % WEIGHT ADDITIVE CONCENTRATE | | | |
| --- | --- | --- | --- |
| Concentrate | F-A | F-B | F-C |
| F-I | 0.08 |  |  |
| F-II |  | 0.07 |  |
| F-III |  |  | 0.1 |
| F-IV |  |  |  |

| UNLEADED GASOLINE + 50 PTB[a] PRODUCT | | | | |
| --- | --- | --- | --- | --- |
| Example | | | | |
| F-D | F-E | F-F | F-G | F-H |
| 4 |  |  |  |  |
|  | 6 |  |  |  |
|  |  | 9 |  |  |
|  |  |  | 17B |  |
|  |  |  |  | 27 |

[a]: adjusted to neat chemical basis

While the invention has been explained in relation to its preferred embodiments, it is to be understood that various modifications thereof will become apparent to those skilled in the art upon reading the specification. Therefore, it is to be understood that the invention disclosed herein is intended to cover such modifications that fall within the scope of the appended claims.

What is claimed is:

1. A lubricating composition comprising a major amount of an oil of lubricating viscosity and a minor amount of a composition prepared by a process comprising first reacting, optionally in the presence of an acidic catalyst selected from the group consisting of organic sulfonic acids, heteropolyacids, Lewis acids, and mineral acids, (A) at least one olefinic compound containing at least one group of the formula $$\begin{matrix} \diagdown & | & | \\ C=C-CH \\ \diagup & & | \end{matrix} \quad (I)$$

wherein the olefinic compound has the general formula $(R^1)(R^2)C=C(R^6)(CH(R^7)(R^8))$ (III) wherein each $R^1$ and $R^2$ is, indepently, hydrogen or hydrocarbon based group, and each of $R^6$, $R^7$ and $R^8$ is, indepently, hydrogen or hydrocarbon based group; and (B) at least one carboxylic reactant selected from the group consisting of compounds of the formula $$R^3C(O)(R^4)_nC(O)OR^5 \quad (IV)$$

and compounds of the formula $$\begin{matrix} R^9O \\ | \\ R^3-C-(R^4)_n-C(O)OR^5 \\ | \\ R^9O \end{matrix} \quad (V)$$

wherein each of $R^3$, $R^5$ and each $R^9$ is independently H or a hydrocarbyl group, $R^4$ is a divalent hydrocarbylene group, and n is 0 or 1, in amounts ranging from 0.6 moles (B) per mole of (A) to 1.5 moles (B) per equivalent of (A); and from about 0.5 to about 2 moles, per mole of (B), of (C) at least one aldehyde or ketone, then reacting the product formed thereby with from about 0.5 equivalents up to about 2 moles, per mole of (B) of at least one of (D) ammonia or a hydrazine or an amine characterized by the presence within its structure of at least one H—N group.

2. The lubricating composition of claim 1 wherein $R^4$ contains from 1 to about 3 carbon atoms.

3. The lubricating composition of claim 1 wherein n=0.

4. The lubricating composition of claim 3 wherein the at least one reactant (B) is glyoxylic acid.

5. The lubricating composition of claim 1 wherein the at least one reactant (B) is the compound of the formula $$\begin{matrix} R^9O \\ | \\ R^3-C-(R^4)_n-C(O)OR^5 \\ | \\ HO \end{matrix} \quad (V)$$

wherein each $R^3$ is H and $R^5$ and $R^9$ are lower alkyl groups selected from the group consisting of methyl, ethyl, propyl and butyl and n=0.

6. The lubricating composition of claim 1 wherein each of $R^1$ and $R^2$ is hydrogen and $R^6$ is H or a lower alkyl group and the group $(CH(R^7)(R^8))$ is a hydrocarbyl group containing from 7 to about 5000 carbon atoms.

7. The lubricating composition of claim 6 wherein the olefinic compound has $\overline{M}_n$ ranging from about 100 to about 70,000.

8. The lubricating composition of claim 6 wherein the group $(CH(R^7)(R^8))$ is an aliphatic group containing from about 30 to about 200 carbon atoms and the olefinic compound is derived from homopolymerized and interpolymerized $C_{2-18}$ olefins.

9. The lubricating composition of claim 8 wherein the group $(CH(R^7)(R^8))$ contains from about 50 to about 100 carbon atoms.

10. The lubricating composition of claim 7 wherein the olefinic compound has $\overline{M}_n$ ranging from about 200 to about 7,000.

11. The lubricating composition of claim 10 wherein the olefinic compound has $\overline{M}_n$ ranging from about 400 to about 3,000.

12. The lubricating composition of claim 8 wherein the olefinic compound is a polyolefin comprising a mixture of isomers, at least about 50% by weight of the mixture comprising isomers of the formula $$H_2C=C(R^6)(CH(R^7)(R^8))$$

wherein $R^6$ is H or lower alkyl.

13. The lubricating composition of claim 12 wherein the polyolefin is a polybutene.

14. The lubricating composition of claim 13 wherein the polybutene is polyisobutylene.

15. The lubricating composition of claim 12 wherein $R^6$ is methyl.

16. The lubricating composition of claim 1 wherein the olefinic compound is a polyolefin comprising a mixture of isomers wherein from about 50% to 65% are trisubstituted olefins wherein one substituent contains from 2 to about 5000 carbon atoms and the other two substituents are lower alkyl.

17. The lubricating composition of claim 16 wherein the trisubstituted olefin composition a mixture of cis-and trans-1-lower alkyl, 1-(aliphatic hydrocarbyl containing from about 30 to about 100 carbon atoms), 2-lower alkyl ethene and 1,1-di-lower alkyl, 2-(aliphatic hydrocarbyl containing from 30 to about 100 carbon atoms) ethene.

18. The lubricating composition of claim 16 wherein the polyolefin is a polybutene.

19. The lubricating composition of claim 18 wherein the polybutene is polyisobutylene.

20. The lubricating composition of claim 1 wherein the olefinic compound is a linear α-olefin containing from 8 to about 28 carbon atoms.

21. The lubricating composition of claim 1 wherein the olefinic compound is an ethylene-alpha-olefin copolymer.

22. The lubricating composition of claim 1 wherein the olefinic compound is an ethylene-alpha olefin-diene terpolymer.

23. The lubricating composition of claim 22 wherein the alpha olefin is a lower olefin and the diene is a non-conjugated diene.

24. The lubricating composition of claim 1 wherein the olefinic compound is a polyolefinic compound.

25. The lubricating composition of claim 1 wherein the olefinic compound is a polydiene polymer.

26. The lubricating composition of claim 1 wherein (C) the aldehyde or ketone is selected from the group consisting of formaldehyde and acetone.

27. The lubricating composition of claim 26 wherein (C) is formaldehyde derived from formalin or paraformaldehyde.

28. The lubricating composition of claim 1 wherein the reaction between (A) and (B) is conducted in the presence of an acid catalyst.

29. The lubricating composition of claim 28 wherein the acid catalyst is selected from the group consisting of a mineral acid and an organic sulfonic acid.

30. The lubricating composition of claim 1 wherein the reaction between (A) and (B) is conducted in the absence of an acidic catalyst.

31. The lubricating composition of claim 1 wherein the reaction between (A) and (B) is conducted in the presence of an azeotroping solvent.

32. The lubricating composition of claim 1 wherein the carboxylic reactant (B) is selected from the group consisting of pyruvic and levulinic acid.

33. The lubricating composition of claim 1 wherein (D) is an alkylene polyamine.

34. The lubricating composition of claim 1 wherein (D) is an alkylene polyamine bottoms product.

35. The lubricating composition of claim 1 wherein (D) is a condensed polyamine derived from at least one hydroxy-containing material and at least one alkylene polyamine or alkylene polyamine bottoms product.

36. The lubricating composition of claim 35 wherein the alkylene polyamine is at least one member of the group consisting of diethylenetriamine, dimethylaminopropylamine diamine, ethylenediamine, and aminoethylpiperazine.

* * * * *

UNITED STATES PATENT AND TRADEMARK OFFICE
CERTIFICATE OF CORRECTION

PATENT NO. : 5,856,279
DATED : January 5, 1999
INVENTOR(S) : Mark R. Baker

It is certified that error appears in the above-indentified patent and that said Letters Patent is hereby corrected as shown below:

Column 31, line 9 Change "indepently" to --independently--

Column 32, line 23 Change "composition" to --comprises--

Signed and Sealed this

Twenty-eighth Day of September, 1999

Attest:

Q. TODD DICKINSON

Attesting Officer    Acting Commissioner of Patents and Trademarks